United States Patent [19]

Ohta

[11] 4,137,413

[45] Jan. 30, 1979

[54] 1,3,7-TRINITROPHENAZINE-5-OXIDE

[75] Inventor: Masafumi Ohta, Tokyo, Japan

[73] Assignee: Ricoh Company, Ltd., Tokyo, Japan

[21] Appl. No.: 809,696

[22] Filed: Jun. 24, 1977

Related U.S. Application Data

[62] Division of Ser. No. 639,417, Dec. 10, 1975, Pat. No. 4,055,421.

[30] Foreign Application Priority Data

Dec. 12, 1974 [JP]  Japan ................................ 49-142736

[51] Int. Cl.$^2$ ............................................. C07D 51/80
[52] U.S. Cl. ...................................... 544/348; 96/1.6
[58] Field of Search ........................ 260/267; 544/348; 96/1.6

[56] References Cited

U.S. PATENT DOCUMENTS 2,986,493  5/1961  Overeem et al. .................... 260/267

FOREIGN PATENT DOCUMENTS 1086522  8/1965  United Kingdom .................... 544/347
1091618  8/1966  United Kingdom .................... 544/347

*Primary Examiner*—Roland E. Martin, Jr.
*Assistant Examiner*—John L. Goodrow
*Attorney, Agent, or Firm*—Blanchard, Flynn, Thiel, Boutell & Tanis

[57] ABSTRACT

The present invention provides 1,3,7-trinitrophenazine-5-oxide which has an excellent sensitization effect on organic photoconductors, as well as a photoconductive sensitive material comprising said compound and an organic photoconductor.

1 Claim, No Drawings

1,3,7-TRINITROPHENAZINE-5-OXIDE

This is a division of application Ser. No. 639,417, filed Dec. 10, 1975, now U.S. Pat. No. 4,055,421.

BACKGROUND OF THE INVENTION

1. Field of the Invention

The present invention relates to 1,3,7-trinitrophenazine-5-oxide which has an excellent sensitization effect on organic photoconductors, as well as a photoconductive sensitive material prepared by combining said compound with an organic photoconductive substance.

2. Description of the Prior Art

Because of their superiority in film formability as well as the transparency and pliability of the film formed thereof, organic photoconductors such as poly-N-vinyl carbazole are coming into the limelight as materials for the purpose of forming the photoconductive layer of electrophotographic copying materials or image-forming elements. However, organic photoconductors are very inferior in photosensitivity to inorganic photoconductors such as zinc oxide, and this has been a major obstacle to putting them to practical use. The present invention is intended to overcome this defect of organic photoconductors, and its principal object is to provide a photosensitive material which is prepared by employing an organic photoconductor, but which nonetheless stands comparison, as regards photosensitivity with photosensitive materials prepared by employing inorganic photoconductors in photosensitivity.

SUMMARY OF THE INVENTION

As the result of a series of studies, the present inventors have found that the employment of 1,3,7-trinitrophenazine-5-oxide having the formula

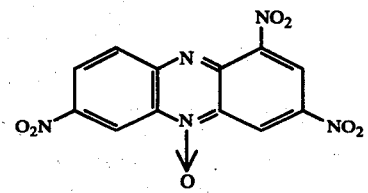

as a sensitizer is very effective for achieving the aforesaid object.

The present invention has been accomplished on the basis of this finding. The present provides a photosensitive material employing said 1,3,7-trinitrophenazine-5-oxide as the sensitizer for organic photoconductors. The present invention also provides said compound as well.

1,3,7-trinitrophenazine-5-oxide is prepared by nitrating phenazine-5-oxide having the formula

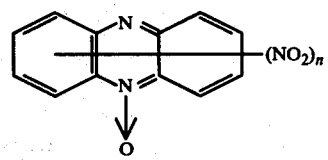

(wherein n is an integer in the range of from 0 to 2) or mononitro derivatives or dinitro derivatives therefrom.

To cite nitro derivatives of phenazine-5-oxide known heretofore there is a disclosure of the mononitro derivatives 1-nitrophenazine-5-oxide and 3-nitrophenazine-5-oxide in Pharm. Bull. (Japan)2(1954)284, and as for dinitro derivative, there is a disclosure 1,7-dinitrophenazine-5-oxide and 3,7-dinitrophenazine-5-oxide in Chem. Pharm. Bull. (Tokyo)6(1958)77. However, as for the trinitro derivative, this has not been reported, and it is believed to be a novel compound.

Hereunder will be given examples the synthesis of this novel compound.

EXAMPLE OF SYNTHESIS 6.0 g of 3,7-dinitrophenazine-5-oxide [which had been synthesized in accordance with Chem. Pharm. Bull. (Tokyo)6(1958) 77] were dissolved in a mixed acid [a liquid mixture consisting of 60 ml of fuming nitric acid (d 1.52) and 60 ml of concentrated sulfuric acid] while cooling with ice. The temperature of this reaction mixture was gradually elevated up to 85° to 90° C. whereat it was maintained for 3.5 hours. Further, after adding thereto another mixed acid [a mixture liquid consisting of 20 ml of concentrated sulfuric acid and 20 ml of fuming nitric acid (d 1.52)] dropwise over about 1 hour's period, the reaction mixture was maintained at a temperature of about 90° to 92° C. for 8 hours. Then, after letting it cool down, the reaction mixture was poured in a large quantity of ice water, the resulting precipitate was separated, washed with water, dried, and thereafter subjected to recrystallization several times by means of benzene, whereby 1.7 g of yellow prismatic crystals were obtained.

The melting point of this product compound was in the range of from 215.5° to 217.0° C. After drying by heating at a temperature of 110° C. for 1 hour, this compound was subjected to the following analysis. As a result of measurement by means of infrared absorption spectrum (employing KBr), there was observed absorptions by aromatic ring at 3080, 1610 and 1585 cm$^{-1}$ and absorptions by nitro group at 1530 and 1340 cm$^{-1}$. By further conducting elementary analysis, the following results was obtained.

| C (%) | H (%) | N (%) |
| --- | --- | --- |
| 43.27 | 1.49 | 21.29 |

The calculated values of trinitrophenazine-5-oxide as $C_{12}H_5N_5O_7$ were as follows:

| C (%) | H (%) | N (%) |
| --- | --- | --- |
| 43.51 | 1.53 | 21.14 |

In the light of the foregoing results, it is concluded that the present compound is trinitrophenazine-5-oxide.

Synthesis Confirmation Test

In order to determine the position of substitution of this trinitro derivative, the following test was conducted.

Nitration of 1,7-dinitrophenazine-5-oxide 0.6 g of 1,7-dinitrophenazine-5-oxide (which had been synthesized on the basis of the same literature as referred to with respect to 3,7-dinitro derivative, was dissolved in a mixed acid [a liquid mixture consisting of 6 ml of fuming nitric acid (d 1.52) and 6 ml of concentrated sulfuric acid] while cooling with ice. The temperature of this reaction mixture was gradually elevated up to 85° to 90° C. whereat it was maintained for 5 hours. Further, after adding thereto another mixed acid [a liquid mixture consisting of 2 ml of concentrated sulfuric acid and 2 ml of fuming nitric acid (d 1.52)] dropwise over about 20 minutes' period, the reaction mixture was maintained at a temperature of about 90° to 92° C. for 5 hours. Then, by processing this reaction mixture in the same way as in the foregoing Example of Synthesis, there was obtained 0.1 g of a compound which did not cause any lowering of the mixed melting point even when mixed with the trinitrophenazine-5-oxide obtained in the Example of Synthesis.

In the light of the foregoing result, it was confirmed that trinitro derivative obtained herein was 1,3,7-trinitrophenazine-5-oxide.

As described hereinabove, 1,3,7-trinitrophenazine-5-oxide is useful as a sensitizer for organic photoconductors. To cite organic photoconductors to which the present compound is applicable, there are the aforesaid poly-N-vinyl carbazole plus various derivatives thereof such as brominated or chlorinated poly-N-vinyl carbazole, nitrated poly-N-vinyl carbazole, polyacenaphthylene, anthracene, pyrene, pyrazolin, imidazole, etc. The 1,3,7-trinitrophenazine-5-oxide employed normally to the extent of 0.01 to 1.3 moles per 1 mole of the organic photoconductor employed (or per 1 monomer unit when the organic photoconductor is a polymer).

The sensitizer according to the present invention can be utilized with the photoconductor for use in electrophotographic copying materials, image-forming elements, etc. as set forth above. The electrophotographic copying material and image-forming element to which the present sensitizer is applicable include all the hitherto known electrophotographic copying materials having a stratiform structure such as conductive support-photoconductive layer; conductive support-inorganic semiconductive layer-photoconductive layer; conductive support-inorganic photoconductive layer-organic photoconductive layer; conductive support-non-sensitizing layer-photoconductive layer; or photoconductive layer-insulating protective film, and image-forming elements also having a stratiform structure such as transparent electrode-ceramics-high molecular film-photoconductive layer-transparent electrode, etc.

As the assistant, the component, the material and the method for formation to be employed for these sensitive materials having stratiform structure, all the hitherto known ones are useful.

For instance, an electrophotographic sensitive material can be prepared through the following process.

The aforesaid organic photoconductor and 1,3,7-trinitrophenazine-5-oxide are dissolved in an organic solvent such as tetrahydrofuran or dioxane thereby to prepare a photoconductive layer forming solution. By coating this solution on the surface of a support having conductivity, such as paper processed for conductivity, a synthetic resin film deposited with aluminum through vacuum evaporation, or a metal sheet like aluminum plate, to the extent of the desired thickness by means of a doctor blade for instance, and drying thereafter, a photoconductive layer is formed on the support. Further, for the purpose of improving the adhesion between the support and the photoconductive layer, polyester resin, acrylic resin, novolak resin and the like are used by adding same to said photoconductive layer forming solution thereby to make a photoconductive layer containing such resins.

In the following will be given examples of the embodiment of the present invention illustrative of the effect of the sensitizer according to the present invention in the case of application thereof to electrophotographic copying materials, but it will be understood that these examples do not mean to limit the scope of the present invention.

DESCRIPTION OF THE PREFERRED EMBODIMENTS

EXAMPLE 1

| | |
|---|---|
| 1,3,7-trinitrophenazine-5-oxide | 660 mg |
| poly-N-vinyl carbazole | 390 mg |
| polyester resin | 91 mg |
| (Polyester Adhesive 49000, the manufacture of Du Pont Co.) | |
| tetrahydrofuran | 8.5 g |

By coating a photoconductive layer forming solution prepared by mixing the above ingredients together on the surface of an aluminum layer formed by depositing aluminum on a polyester film through vacuum evaporation by means of a doctor blade having a gap of 200μ, followed by 10 minutes' drying at a temperature of 60° C. and 2 minutes' drying at a temperature of 120° C., an electrophotographic sensitive material having an about 10 μ-thick photoconductive layer was obtained.

The thus obtained photosensitive material was halved, and the respective halves were electrified by corona discharge of $-6$ KV or $+6$ KV for 20 seconds by employing a commercial electrostatic copying machine, left standing in the dark for 20 seconds thereafter, and measured for their surface potential VPo (V) at that time. Subsequently, said halves were exposed to the light of a tungsten lamp to the extent of a surface illumination of 20 luxes. The attenuation of the surface potential at that time and the time required therefor were recorded by a recorder, and the time (in terms of seconds) required for attenuation of VPo to half was calculated to determine the amount of exposure E ½ in terms of 20 lux × second. In other words, E ½ expresses the amount of exposure required for attenuation of VPo to ½ and is indicative of the sensitivity of the photosensitive material. The values of VPo and E ½ (lux·sec) obtained through the above procedure were as follows:

| electric charge | VPo | E ½ |
|---|---|---|
| − | 640 | 3.8 |
| + | 350 | 9.6 |

Further, by using an electrophotographic sensitive material prepared as above, charging the photoconductive layer thereof with negative electricity by means of a commercial electrophotographic copying machine, subjecting it to exposure thereafter through an image-carrying original thereby to form an electrostatic latent image on the photoconductive layer thereof, developing said latent image with a commercial powder developer charged with positive electricity, superposing a transfer paper on the thus developed image, imparting said image with negative electricity by way of said transfer paper by employing the aforesaid copying machine again thereby to transfer the image formed by the developer onto the transfer paper, and then heating, the image was fixed on the transfer paper. The image thus formed on the transfer paper had a high contrast as well as concentration and proved to be a copy of superior quality.

Comparative Example

After preparing a photosensitive material by employing 630 mg of 2,4,7-trinitrofluorenone disclosed in U.S. Pat. No. 3,484,237 in place of 660 mg of 1,3,7-trinitrophenazine-5-oxide used in Example 1, by employing the same procedure as that in Example 1, VPo and E ½ (lux·sec) were measured. The result was as follows:

| electric charge | VPo | E ½ |
|---|---|---|
| — | 530 | 4.6 |

As verified by this result, the photosensitive material according to the present invention can be charged with more electricity and is higher in sensitivity than this comparative photosensitive material.

EXAMPLES 2-4

After preparing a variety of electrophotographic sensitive materials by employing the same procedure as that in Example 1, except that 1,3,7-trinitrophenazine-5-oxide and organic photoconductor were employed in the respective amounts shown in the following Table-1 and employing the same polyester resin and tetrahydrofuran as used in Example 1 in the respective amounts shown in said Table-1, by using the respective photosensitive materials and employing the same procedure as that in Example 1, electrification and exposure were conducted, and VPo and E ½ were measured. The values of VPo and E ½ thus obtained were as shown in the following Table-2.

Table-1

| No. | 1,3,7-trinitro-phenozine-5-oxide | Organic photoconductor | Polyester resin (polyester Adhesive 49000) | Tetrahydrofuran |
|---|---|---|---|---|
| 2 | 660 mg | *chlorinated poly-N-vinyl carbazole 460 mg | 0 mg | 8.5 g |
| 3 | 490 mg | **brominated poly-N-vinyl carbazole 500 mg | 90 mg | 8.0 g |
| 4 | 160 mg | 1-bromopyrene formaldehyde resin 570 mg | 260 mg | 5.8 g |

Remarks: *Compound obtained by substituting 1 chlorine atom per 1 monomer unit of poly-N-vinyl carbazole.
**Compound obtained by substituting 1 bromine atom per 2 monomer units of poly-N-vinyl carbazole.

Table-2

| Example No. | & | Electric Charge | VPo (V) | E ½ (lux . sec) |
|---|---|---|---|---|
| 2 | | — | 850 | 4.4 |
| 3 | | — | 820 | 5.1 |
| 4 | | — | 940 | 11.3 |

As verified by this result, it is possible to prepare electrophotographic sensitive materials utilizing organic photoconductors which will bear comparison, in terms of photosensitivity, with electrophotographic sensitive materials utilizing inorganic photoconductors by forming their photoconductive layer from a composition comprising 1,3,7-trinitrophenazine-5-oxide admixed with an organic photoconductor.

What is claimed is:
1. 1,3,7-trinitrophenazine-5-oxide.

* * * * *